(12) United States Patent
Wilson

(10) Patent No.: US 8,652,463 B1
(45) Date of Patent: Feb. 18, 2014

(54) DIETARY SUPPLEMENT TO REDUCE THE OCCURRENCE OF MIGRAINES AND TREAT THEIR SYMPTOMS

(76) Inventor: Robert Wilson, Tampa, FL (US)

( * ) Notice: Subject to any disclaimer, the term of this patent is extended or adjusted under 35 U.S.C. 154(b) by 317 days.

(21) Appl. No.: 13/077,109

(22) Filed: Mar. 31, 2011

(51) Int. Cl.
*A61K 38/43* (2006.01)

(52) U.S. Cl.
USPC ............................................. 424/94.1

(58) Field of Classification Search
USPC ........................................... 424/94.1
See application file for complete search history.

(56) References Cited

U.S. PATENT DOCUMENTS

| | | | |
|---|---|---|---|
| 6,068,999 | A | 5/2000 | Hendrix |
| 6,159,505 | A | 12/2000 | Piper |
| 6,465,517 | B1 | 10/2002 | Van Der Zee |
| 6,500,450 | B1 | 12/2002 | Hendrix |
| 7,335,384 | B2 | 2/2008 | Khaled |
| 2004/0048870 | A1 | 3/2004 | Amir et al. |
| 2006/0233892 | A1* | 10/2006 | Hendrix ..................... 424/702 |
| 2010/0284986 | A1* | 11/2010 | Kelleher ................... 424/94.1 |

OTHER PUBLICATIONS

Morris Maizels MD, et al. A Combination of Riboflavin, Magnesium, and Fever for Migraine Prophylaxis: A Randomized Trial Headache: The Journal of Head and Face Pain vol. 44 Issue 9 pp. 885-890, Sep. 22, 2004.
Lida R. Etemad, PharmD, et al. Costs and Utilization of Triptan Users Who Receive Drug Prophylaxis for Migraine Versus Triptan Users Who Do Not Receive Drug Prophylaxis Journal of Managed Care Pharmacy vol. 11 No. 2, Mar. 2005.
Suzanna C. MacLennan, et al. High-Dose Ribof lavin for Migraine Prophylaxis in Children: A Double Blind, Randomized, Placebo-Controlled Trial vol. 23 No. 11 Nov. 2008.
Juanita Rios, RN, MSN, FNP, et al. Evidenced-Based Use of Botanicals, Minerals, and Vitamins in the Prophylactic Treatment of Migraines Journal of the American Academy of Nurse Practitioners vol. 16 Issue 6, Jun. 2005.
B. Lee Peterlin, DO, et al. Rational Combination Therapy in Refractory Migraine Headache:The Journal of Head and Face Pain vol. 48 Issue 6 pp. 805-819, Jun. 2, 2008 .
Andrew D. Hershey, MD, et al. Coenzyme Q10 Deficiency and Response to Supplementation in Pediatric and Adolescent Migraine The Journal of Head and Face Pain vol. 47 Issue 1, Jan. 15, 2007.
Richard G. Boles, et al. Treatment of cyclic vomiting syndrome with co-enzyme Q10 and amitriptyline, a retrospective study BMC Neurol vol. 10 Jan. 2010.
TD Rozen, et al. Open Label trial of coenzyme Q10 as a migraine preventive Cephalalgia vol. 22 Issue 2, Apr. 2002.
Stephen D. Siberstein MD et al. Pharmacological Approaches to Managing Migraine and Associated Comorbidities—Clinical Consideration for Monotherapy Versus Polytherapy Headache: The Journal of Head and Face Pain vol. 47, Apr. 13, 2007.
Pedro A. Kowacs MD et al Rejection and Acceptance of Possible Side Effects of Migraine Prophylactic Drugs Headache: The Journal of Head and Face Pain vol. 49 Issue 7, Apr. 28, 2009.
Peter S. Sandor MD, et al. Prophylactic Treatment of Migraine With B-Blockers and Riboflavin: Differential Effects on the Intensity Dependence of Auditory Evoked Cortical Potentials Headache: The Journal of Head and Face Pain vol. 40, Jan. 2000.
P-HM Van Der Kuy, et al. Hydroxocabalamin, a nitric oxide scavenger, in the prophylaxis of migraine: an open, pilot study Cephalalgia, vol. 22 No. 7 Sep. 2002.
Randolph W. Evans, MD, et al. "Natural" or Alternative Medications for Migraine Prevention Headache: The Journal of Head and Face Pain vol. 46 Issue 6, May 24, 2006.
Dorethea S. Franca B Vitamins induce an antinociceptive effect in the acetic acid and formaldehyde models of nociception in mice European Journal of Pharmacology vol. 421 Issue 3, Jun. 15, 2001.
M. Sparaco et al. Mitochondrial dysfunction and migraine: evidence and hypotheses Cephalalgia vol. 26 Issue 4, Dec. 6, 2005.
Stewart J. Tepper, MD. Complementary and Alternative Treatments for Childhood Headaches Current Pain and Headache Reports 2008 12:379-383.
Alan M. Rapoport Acute Treatment of Headache J Headache Pain 2006 7:355-359.
Lawrence D. Goldberg, MD MBA The American Journal of Managed Care The Cost of Migraine and Its Treatment Jun. 15, 2005.
Chiaki Isobe, MD et al. A Remarkable Increase in Total Homocysteine Concentrations in the CSF of Migraine Patients With Aura Nov. 3, 2010.
Richard B. Lipton , MD et al. In-office Discussions of Migraine: Results from the American Migraine Communication Study vol. 23 p. 8 Aug. 2008.
Jan Lewis Brandes MD The Migraine Cycle: Patients burden of Migraine During and Between Migraine Attacks Headache: The Journal of Head and Face Pain vol. 48 Issue 3, 2007.
Curtis P. Schreiber, MD, et al. Prevalence of Migraine in Patients With History of Self-reported or Physician-Diagnosed "Sinus" Headache Archives of Internal Medicine vol. 164 No. 16, 2004.
Alfredo Bianchi, et al. Role of Magnesium, Coenzyme q10, Riboflavin, and Vitamin B12 in Migraine Prophylaxis Vitamins and Hormones vol. 69 Copyright 2004, Elsevier Inc.
Roger K. Cady, MD. The Future of Migraine: Beyond Just Another Pill Mayo Clinic Proceedings 2009.
Bverly S. Tozer, MD, et al. Prevention of Migraine in Women Throughout the Life Span Mayo Clinic Proceedings 2006.

* cited by examiner

*Primary Examiner* — Jon P Weber
*Assistant Examiner* — Kara Johnson
(74) *Attorney, Agent, or Firm* — Goldstein Law Offices, P.C.

(57) ABSTRACT

A method of treatment to reduce the frequency of migraine headaches and lessen the severity of associated symptoms by a daily intake of a combination of dietary supplements, namely riboflavin, magnesium, vitamin B12 and coenzyme Q10. The preferred daily dosage of the invention is riboflavin, 50 mg; magnesium, 400 mg as elemental magnesium; vitamin B12, 1000 µg; and coenzyme Q10, 50 mg. The magnesium is preferably in the form of magnesium oxide. The dietary supplements are generally recognized as safe for human consumption. The four dietary supplements synergistically act together at the preferred dosage ranges and are uniquely suited for preventing and reducing the occurrence of migraine headaches and associated symptoms.

2 Claims, 1 Drawing Sheet

DIETARY SUPPLEMENT TO REDUCE THE OCCURRENCE OF MIGRAINES AND TREAT THEIR SYMPTOMS

BACKGROUND OF THE INVENTION

The invention relates generally to a combination of dietary supplements for preventing migraine headaches. More particularly, the invention relates to a combination of dietary supplements and a method of treatment with the combination of dietary supplements for preventing and reducing an occurrence of a migraine headache and a plurality of associated symptoms of migraine headaches.

Migraine is a potentially chronic, progressive and pervasive disease that erodes the sufferer's daily quality of life and as well as substantially affecting patients' families, workplaces and society. Historically, migraine has been characterized as episodic attacks separated by normal, symptom-free periods. Findings from migraine sufferers surveyed in a national poll revealed that migraineurs do not view their migraines as isolated events. These sufferers consider their migraines part of a cycle of suffering, treating their current attack and worrying about when the next attack will strike. (J. L. Brandes, Headache: The Journal of Head and Face Pain; Vol. 48, p. 430-441, March 2008)

Migraines are more prevalent in women than men at almost a three to one ratio, associated with mainly the hormone milieu of the reproductive years. The overwhelming majority, more than four-fifths of self-diagnosed or physician diagnosed sufferers of "sinus" headaches actually meet the criteria for migraine headaches. Migraine is under-recognized and under diagnosed. (Curtis Schreiber et al., Archives Int. Med. Vol. 164, No. 16, Sep. 13, 2004)

The medical community, in recognizing the chronic and progressive nature of migraine, can focus on prevention or reversal of disease progression. Less than five percent of migraine sufferers receive preventive therapy. Most in-office visits do not result in significant information exchanged between doctor and patient about the severity of headaches or the degree of impairment. Candidates for preventive therapy often leave office without discussion or receiving preventive medication. (Richard B. Lipton et al., J. Gen Intern Med. 2008 August; 23(8): 1145-1151.) Non-pharmacological prevention focuses on avoiding migraine food triggers, a healthy lifestyle with adequate sleep and exercise, biofeedback and relaxation. Preventive medications that the Food and Drug Administration has approved include antiepileptic drugs topiramate and divalproate sodium for migraine prophylaxis. However, other antiepileptic drugs do not work and are not approved for this indication. (Roger Cady, Mayo Clin. Proc., May 2009; 84(5):397-399) Another approach to prophylaxis is the use of botulinum toxin, which incurs minimal systemic side effects and does not rely on daily patient compliance. Botulinum toxin was discovered to have a high affinity to the neuromuscular junction, inhibiting release of adenosine. Botulinum toxin Type A was reported in reducing the number of headache days in patients.

Efficacy of preventive therapy is defined as greater than a fifty percent reduction in migraine frequency. Fifty percent of patients do not respond to preventive medication. Beneficial effects of preventive medication may be reduced by abuse of other medications during treatment of an acute attack. (Beverly Tozer et al., Mayo Clin. Proc., August 2006; 81(8):1086-1092)

Effective migraine preventive therapy should decrease the frequency, severity, and duration of migraines, thereby helping to less the cycle of migraine and possibly prevent or reduce chronicity. Patients receiving drug prophylaxis had lower migraine-related costs than using acute treatment alone. A large segment of patients remain under-treated. (Brandes, Id.)

Migraine is also associated with both comorbid and concomitant illnesses that influence treatment strategy. Comorbid illness include depression, anxiety, epilepsy, sleep disorders, stroke; concomitant disorders include hypertension and obesity. Polytherapy, that is treating each disorder as a separate indication, increases the likelihood and the danger of interactions. Patients are not accepting of side effects from multiple medications and drop one or more drugs from their regimen. Monotherapy, that is a single agent that covers migraine and comorbid conditions, requires choosing the right drug, dosage and regimen, which may result in a less than effective migraine preventive treatment method.

Drugs approved for migraine prophylaxis include the beta blockers propranolol and timolol and the antiepileptic drugs divalproex and topiramate discussed previously. Drugs used off-label for prophylaxis include other agents of the beta blocker and anticonvulsant classes, calcium channel blockers, and antidepressants (e.g., tricyclics and selective serotonin re-uptake inhibitors). (Lawrence D. Goldberg; Am J Manag Care. 2005; 11:S62-S67)

Several theories have been proposed for the etiology of migraine headaches. One theory, dating back to 1938 from Graham and Wolff attribute migraines to vasoconstriction followed by vasodilation. Modern blood flow imaging techniques have shown that this does not fit the typical course of a migraine. It has also been theorized that certain physical and chemical agents act as triggers. Researchers know that migraines run in families, indicating a strong genetic component to the etiology, and although no specific genetic markers have been identified, some have been implicated.

The current thinking includes a theory by Moskowitz that involves the trigeminovascular complex, where neurons release substance P and nitric oxide causing neurogenic inflammation of the meninges causing the migraine headache and associated symptoms. (Alfredo Bianchi et al., Vitamins and Hormones, Vol. 69 2004 p. 297-312)

Migraineurs have been found to have lower magnesium levels in the red blood cells and brain during a migraine. A mitochondrial dysfunction resulting in impaired oxygen metabolism has been suggested for migraine pathogenesis. It has been reported that a defect of reduced NADH (nicotinamide adenine dinucleotide dehydrogenase) in the mitochondria as well as citrate synthase and cytochrome-c-oxidase platelet activity. Mitochondria play a dominant role during cellular respiration in the production of ATP (adenosine-5'-triphosphate) that is responsible for the transfer of energy by electron transport from cell to cell. This is done by oxidizing the major products of glucose, pyruvate, and NADH. Some studies have shown an impaired energy metabolism in brain and skeletal muscle in migraine patients. Patients have demonstrated a reduction in mitochondrial phosphorylation potential in between attacks, further interfering with the cellular electron transport chain. (Bianchi, Id.)

Migraineurs who suffer from migraine with aura have a significant increase of total homocysteine in cerebrospinal fluid compared to the normal population. (Isobe and Terayama, Headache: J Head and Face Pain, Vol. 50 No. 10 p 1561-1569.) Hyperhomocysteinemia is a medical condition characterized by a high levels of homocysteine, which may lead to an excessive production of homocysteic acid, a toxin that possess strong excitatory effects on neurons. Homocysteic acid could sensitize the cerebral arteries and active the trigeminovascular system, predisposing a patient to migraine attacks. (Bianchi, Id.)

Many have proposed individual or combinations of dietary supplements as preventive treatment of migraines. Amir and Amir (U.S. Patent Application Publication 2004/0048870) propose a combination of magnesium in a range of 100 to 800 mg with 200 mg as preferred dosage and riboflavin in a range 100 to 600 mg with 400 mg as preferred dosage). Amir and Amir also propose combining magnesium and riboflavin with calcium, as well as a further combination with calcium and Vitamin D. Amir and Amir do not propose other vitamins, in particular other B vitamins, in combination with magnesium and riboflavin.

In U.S. Pat. No. 7,335,384, Khaled propose a combination of riboflavin, pyridoxine, cobalamin, magnesium, glucosamine sulfate, methylsulfonylmethane and coenzyme Q-10 in wide ranges of therapeutic levels in further combination with beta carotene, thiamine HCl, ascorbic acid, folate, biotin, vitamin E, zinc, selenium, manganese, glutathione, niacinamide, N-acetyl-tyrosine, α-lipoic acid, hydroxycitric acid, S-adenosylmethionine, pantothenic acid, and chondroitin sulfate for the prevention and treatment of migraine and other disease states and conditions associated with neurogenic inflammation.

In U.S. Pat. No. 6,500,450, Hendrix teaches an extract of the feverfew plant containing parthenolide in combination with magnesium, as a combination of magnesium oxide and a magnesium salt of an organic acid with or without riboflavin as a method of reducing the number of migraine headaches and associated symptoms. Previously in U.S. Pat. No. 6,068,999, Hendrix proposed that the ratio of the magnesium oxide to a magnesium salt of citric acid is 1:1 in combination with parthenolide, with or without riboflavin.

In U.S. Pat. No. 6,465,517, Van Der Zee proposes a composition comprising taurine, coenzyme Q10 and additionally creatine, L-carnitine, certain vitamins and minerals, carbohydrates, proteins, fats and herbal extracts for the treatment, not prevention of migraines. Van Der Zee does not include in the composition most water-soluble vitamins, only riboflavin, thiamine and ascorbic acid.

Piper has proposed in U.S. Pat. No. 6,159,505 several compositions and methods for the treatment and prevention of migraine or stress headaches. Piper teaches a combination of potassium, magnesium and pyridoxine (Vitamin $B_6$) and optionally further combines the magnesium and pyridoxine ingredients with other common vitamins and minerals in a typical multivitamin preparation and still further adds a simple analgesic to the method of treatment.

While these compositions and methods may be suitable for the particular purpose employed, or for general use, they would not be as suitable for the purposes of the present invention as disclosed hereafter.

SUMMARY OF THE INVENTION

The invention is a method of treatment to prevent or reduce the frequency of migraine headaches and lessen the severity of associated symptoms by a daily intake of a combination of dietary supplements, namely riboflavin, magnesium, vitamin $B_{12}$ and coenzyme Q10. The preferred daily dosage of the invention is riboflavin, 50 mg; magnesium, 400 mg as elemental magnesium; vitamin $B_{12}$, 1000 μg; and coenzyme Q10, 50 mg. The magnesium is preferably in the form of magnesium oxide. The dietary supplements are generally recognized as safe for human consumption.

The combination of dietary supplements and the method of treatment have heretofore been lacking in the art. The four dietary supplements synergistically act together at the preferred dosage ranges and are uniquely suited for preventing and reducing the occurrence of migraine headaches and associated symptoms.

To the accomplishment of the above the invention may be embodied in the form described hereinbelow. Variations are contemplated as being part of the invention, limited only by the scope of the claims.

BRIEF DESCRIPTION OF THE DRAWINGS

The drawings are briefly described as follows.

DETAILED DESCRIPTION OF THE PREFERRED EMBODIMENTS

Figures 1, 2, 3:
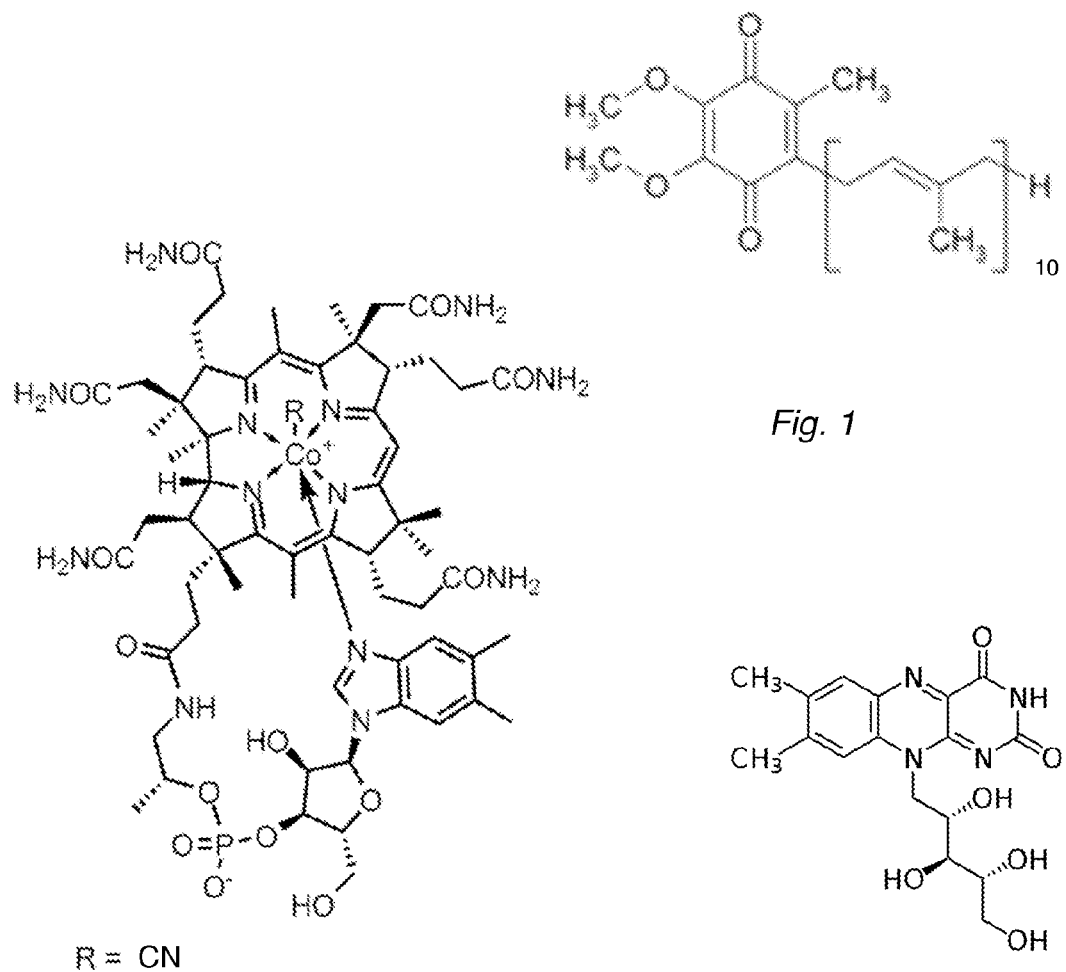
FIG. 1 is a diagram of the chemical structure of coenzyme Q10.
FIG. 2 is a diagram of the chemical structure of Vitamin $B_{12}$.
FIG. 3 is a diagram of the chemical structure of riboflavin.

The invention is a method of treatment to prevent or reduce the frequency of migraine headaches and lessen the severity of associated symptoms of migraine headache by a daily intake of a combination of dietary supplements, namely riboflavin, magnesium, vitamin $B_{12}$ and coenzyme Q10. The four dietary supplements synergistically act together, each at a preferred daily dosage range. Each has a unique role in preventing and reducing the occurrence of migraine headaches and associated symptoms; however, when taken in combination with each other, there is an increase in the preventive effectiveness by the combined multiple actions of the four supplements. The supplements have a proposed method of action at a subcellular level of preventing mitochondrial damage, promoting energy transfer through electron transfer within the mitochondria, stabilizing cell membranes, and scavenging and controlling the release of nitric oxide.

FIG. 1 is a representation of the structure of coenzyme Q10. Coenzyme Q10 is also called ubiquinone, ubidecarenone, coenzyme Q, and abbreviated as CoQ10, CoQ, Q10, or Q. The Chemical Abstracts Service (CAS) has assigned CAS No. 303-98-0 to the compound. Coenzyme Q10 protects mitochondria from free radical damage. Coenzyme Q10 has been shown to improve brain and muscle energy metabolism in the electron transfer process and plays a role in the permeability of the inner mitochondrial membrane. (Bianchi, Id.)

In the preferred embodiment, the daily dosage range of coenzyme Q10 is 42 mg to 75 mg, the range typical of a commercially available form of coenzyme Q10 with a nominally labeled value of 50 mg. The preferred daily dosage range is 45 mg to 60 mg and the preferred daily dose is about 50 mg. Coenzyme Q10 is taken either in combination with one or more of the dietary supplements of the invention, or in a separate dosage form, or in combination with other dietary supplements. Coenzyme Q10 is safe with little or no side effects at the daily range of the invention.

Magnesium counteracts vasospasm, inhibiting platelet aggregation and stabilizing cell membranes, effects serotonin receptors, nitric oxide synthesis and release, inflammatory mediators, and a variety of other migraine-related receptors and neurotransmitters. (Bianchi, Id.) Stabilizing cell membranes including the mitochondrial membranes promotes electron transfer within the cell preventing faulty oxygen metabolism within the cell during cell respiration, a condition associated with migraines.

In the preferred embodiment, magnesium is in the preferred form of magnesium oxide, also known as magnesia, CAS No. 1309-48-4. However, other forms of magnesium, such as magnesium salts can be substituted or combined with magnesium oxide, providing in combination the preferred dose of elemental magnesium of the invention. The source of magnesium is selected from magnesium oxide, and a group of magnesium salts such as magnesium citrate, magnesium glycinate and magnesium pidolate. Magnesium oxide is preferable for its low incidence of adverse experiences.

In the preferred embodiment, the daily dosage range of magnesium is 300 mg to 500 mg, the range typical of a commercially available form of magnesium, calculated on an elemental magnesium basis with a nominally labeled value of 400 mg. The preferred daily dosage range is 360 mg to 440 mg and the preferred daily dose is about 400 mg, calculated on the elemental magnesium basis. Magnesium as a salt or preferably as magnesium oxide is taken either in combination with one or more of the dietary supplements of the invention, or in a separate dosage form, or in combination with other dietary supplements. Magnesium, especially magnesium oxide, is safe with little or no side effects at the daily range of the invention.

FIG. 3 is a representation of the structure of riboflavin, also known as vitamin $B_2$, and has the CAS No. 83-88-5. Riboflavin is an essential constituent and precursor to riboflavin 5'phosphate, which is required for activity of flavoenzymes involved in the electron transport chain. Altered mitochondrial energy metabolism has been implicated in migraine pathogenesis. Riboflavin as a precursor in the electron transport chain may increase the efficiency of energy metabolism within the mitochondria. Riboflavin also can function as a vitamin $B_{12}$ precursor (Bianchi, Id.)

In the preferred embodiment, the daily dosage range of riboflavin is 42 mg to 75 mg, the range typical of a commercially available form of riboflavin with a nominally labeled value of 50 mg. The preferred daily dosage range is 45 mg to 60 mg and the preferred daily dose is about 50 mg. Riboflavin is taken either in combination with one or more of the dietary supplements of the invention, or in a separate dosage form, or in combination with other dietary supplements. Riboflavin is safe with little or no side effects at the daily range of the invention, while minor side effects have been reported at much higher doses when riboflavin was used alone in a migraine prophylaxis study.

FIG. 2 is a representation of the structure of vitamin $B_{12}$, also known as cobalamins, and has the CAS No. 68-19-9. One of the associated symptoms of migraine is gastric distress, which decreases intrinsic factor which is necessary for the biosynthesis of vitamin $B_{12}$. Vitamin $B_{12}$ deficiency is also associated with hyperhomocysteinemia, which has been found comorbid with migraineurs. Vitamin $B_{12}$ acts as a scavenger for nitric oxide, which is believed to play a role in pain generation and transmission in the central nervous system and inhibits the cellular respiratory chain. Vitamin $B_{12}$ also improves the production of ATP (adenosine triphosphate), which increase the electron transport chain. Additionally, riboflavin, as described above, can function as a vitamin $B_{12}$ precursor, synergistically increasing the amount of available vitamin $B_{12}$, and improving mitochondrial function through the increase in vitamin $B_{12}$ as well as playing its own role in electron transport.

In the preferred embodiment, the daily dosage range of vitamin $B_{12}$ is 850 µg to 1500 µg, the range typical of a commercially available form of vitamin $B_{12}$ with a nominally labeled value of 1000 µg (1 mg). The preferred daily dosage range is 950 µg to 1100 µg and the preferred daily dose is about 1000 µg (1 mg). Vitamin $B_{12}$ is taken either in combination with one or more of the dietary supplements of the invention, or in a separate dosage form, or in combination with other dietary supplements. Vitamin $B_{12}$ is safe with little or no side effects at the daily range of the invention.

The following table lists the daily dosage range for each of the dietary supplements of the invention, the preferred daily dosage range for each as well as the preferred dose.

TABLE 1

| Supplement | Daily Range | Preferred Daily Range | Preferred Daily Dosage |
|---|---|---|---|
| Riboflavin | 42 mg-75 mg | 45 mg-60 mg | 50 mg |
| Magnesium | 300 mg-500 mg | 360 mg-440 mg | 400 mg |
| Vitamin $B_{12}$ | 850 µg-1500 µg | 950 µg-1100 µg | 1000 µg |
| Coenzyme Q10 | 42 mg-75 mg | 45 mg-60 mg | 50 mg |

Example 1

Patient GT, a 28 year old female presented with a history of migraines starting in adolescence that predates her eight year history of multiple sclerosis (MS). The patient has a family history of migraines. Her MS is stable, with some muscle fatigue and is well controlled by daily subcutaneous BETASERON® 0.3 mg (BETASERON® is the registered trademark of Bayer Schering Pharma AG, Berlin, Germany). Additionally, the patient takes 2,000 I.U. vitamin D orally daily. The patient's migraines are with and without visual aura along with associated symptoms of photophobia, phonophobia, nausea with and without emesis, and inability to carry out activities of living. Her activities of living include homemaking and home schooling her three children. She sought out neurological care for worsening migraines, the frequency of migraines have escalated from twice a month to six to eight times a month. The patient has not responded without side effects to rescue agents for acute migraine such as triptans, a family of tryptamine-based drugs that are serotonin receptor agonists. She also voiced concern about using conventional migraine preventives due to worry over side effects of fatigue and cognitive dysfunction and impairment. The patient started the method of treatment of the invention by daily doses every morning of the following: coenzyme Q10, 50 mg; vitamin $B_{12}$ 1,000 µg; magnesium, 400 mg; and riboflavin, 50 mg. The patient returned to the outpatient clinic at two months and four months after starting the regimen with a marked return to baseline migraine frequency of twice per month, with a reduction of the severity of the migraine associated symptoms without any reported side effects.

Example 2

Patient PS is a 33 year old female with a nine year history of migraines. She has had numerous neurological consultations for her migraines. Historically, she has six to eight migraines per month. Additionally, her migraines degenerate into status migrainosus migraine (greater than 72 hour duration). The migraines have caused worked to be missed. She has tried IMITREX® (IMITREX® is the registered trademark of Glaxo Group, LTD. Greenford, Middlesex, UK), MAXALT® (MAXALT® is the registered trademark of Merck & Co., Inc., Whitehouse Station, N.J.), PERCOCET®

(PERCOCET® is the registered trademark of Endo Pharmaceuticals, Inc., Chadds Ford, Pa.), VICODIN® (VICODIN® is the registered trademark of Abbott Laboratories, Abbott Park, Ill.), TORADOL® (TORADOL® is the registered trademark of Majedo Corp, Houston, Tex.), or FIORICET® (FIORICET® is the registered trademark of Watson Pharmaceuticals, Inc., Corona, Calif.) with poor response for acute migraine rescue. IMITREX® worked well initially, but became ineffective. She has used individually TOPAMAX® (TOPAMAX® is the registered trademark of Johnson & Johnson, New Brunswick, N.J.), ELAVIL® (ELAVIL® is the registered trademark of Zeneca, Inc. Wilmington, Del.), and ZANAFLEX® (ZANAFLEX® is the registered trademark of Acorda Therapeutics, Inc., Hawthorne, N.Y.) for migraine prevention, but had to stop because of cognitive dysfunction secondary to these medications' side effects. The patient started using chemodenervation with BOTOX® botulinum toxin (BOTOX® is the registered trademark of Allergan, Inc., Irvine Calif.) 100 units injections (20 units into the frontalis, 10 units into the corrugator, 10 units into each temporalis muscles, and remaining 50 units into the suboccipital musculature. BOTOX® injections provided complete remission of migraines to once per month and good response to abortive therapy of TORADOL® 10 mg orally as needed. BOTOX® offered migraine remission despite the discomfort and inconvenience of seventeen to twenty injections during BOTOX® treatment. Four years later, BOTOX® was stopped due to pregnancy planning. In the subsequent year, the patient had an uncomplicated pregnancy also associated with few migraines. Postpartum, she had a recurrence of migraine frequency and severity as previous to her pregnancy, and sought preventative alternatives to BOTOX®, which was no longer covered by health insurance. The patient started the method of treatment of the invention by daily doses every morning of the following: coenzyme Q10, 50 mg; vitamin $B_{12}$ 1,000 µg; magnesium, 400 mg; and riboflavin, 50 mg. Her migraines with the regimen placed her in remission again without side effects. She continues to do well with migraine control on the stated regimen, except for an interval when she was inconsistent in following the regimen. This inconsistency led to an increase in migraine severity and frequency. By returning to the method of treatment with stable and consistent dosing, her migraines are stable and infrequent.

Example 3

Patient KJ is a 32 year old female with a five year history of migraines, with a frequency of seven times a month before treatment with the method of the invention. Her migraines are associated with nausea with emesis, visual aura, photophobia and phonophobia. She has missed worked and has limited her social activities due to the disabling quality of her migraines. She carries a comorbid diagnosis of asthma, controlled on albuterol, and stable Type 2 bipolar disorder, well controlled on BUSPAR® and XANAX® as needed. (BUSPAR® is the registered trademark of Bristol-Myers Squibb Company, New York, N.Y. and XANAX® is the registered trademark of Pharmacia & Upjohn Company, LLC, Peapack, N.J.) With the coexisting conditions, she has little or no preventive treatment options. She has had poor tolerance and poor migraine reduction and severity with TOPAMAX® and other anticonvulsants. Anticonvulsants caused fatigue, depression, and cognitive dysfunction. A beta blocker is contraindicated with asthma and tricyclic antidepressants are contraindicated when there is a potential for worsening bipolar disorder. Additionally, with her low blood pressure, it is not advisable to use a calcium channel blocker for migraine prevention. Economics and health insurance rule out BOTOX® injections and chemodenervation. Historically, she has used FROVA®, PERCOCET® (FROVA® and PERCOCET® are the registered trademarks of Endo Pharmaceuticals, Inc., Chadds Ford, Pa.) and phenegran for acute migraine with moderate success. Two years ago, the patient started the method of treatment of the invention by daily doses of the following: coenzyme Q10, 50 mg; vitamin $B_{12}$ 1,000 µg; magnesium, 400 mg; and riboflavin, 50 mg. Currently the frequency of her migraines is reduced to two migraines per month and only requires FROVA® as a rescue drug with success when using the regimen stated hereinabove.

Example 4

Patient WR is a 40 year old female architect, who sought out neurological consultation to worsening migraines. Her migraines started six years previously, but had worsened in severity and frequency. She has missed work due to the disabling quality of the migraines with head pain, mental exhaustion, and fatigue due to the impact of migraine. She is cautious about trying any preventives over concern of cognitive side effects, particularly because of her work responsibilities. The patient started the method of treatment of the invention by daily doses of the following: coenzyme Q10, 50 mg; vitamin $B_{12}$ 1,000 µg; magnesium, 400 mg; and riboflavin, 50 mg. After two years later using the regimen stated hereinabove, she reports her migraines are in remission. The migraines no longer have not affected her ability to work and respond to the over the counter medication EXCEDRIN® (EXCEDRIN® is registered trademark of Novartis AG, Basel, Switzerland) for acute, abortive therapy. She only has one to two migraines per month and has not invested economic cost or time in any other migraine therapy.

Example 5

Patient RG is 50 year old female, diagnosed with multiple sclerosis (MS) 15 years ago after evaluation of aphasia. Patient had been a migraineur many decades before MS diagnosis with a strong family history of migraines, including a daughter who also suffers from migraines. The patient's migraines historically occur four times per month without clear migraine triggers. She has used ZOMIG® 5 mg (ZOMIG is the registered trademark of IPR Pharmaceuticals, Inc., Carolina, PR) and EXCEDRIN® together to abort the acute migraine. She has been on ELAVIL® in the past for migraine prevention, but problematic secondary to fatigue issues. Her MS has been well controlled on AVONEX® 20 µg intramuscular injections weekly (AVONEX® is the registered trademark of Biogen Idec Inc., Weston, Mass.). Her only issue related to MS is occasional mental exhaustion and lassitude. She has not had flare up or attack of clinical concern related to MS in over a decade. She did partake in a two year clinical study, changing AVONEX® to BETASERON® 0.3 mg subcutaneous every other day, five to six years ago. Three years ago, her migraines worsened in frequency and severity during the onset of menopause with a disabling quality. She has missed work as a health care professional because of the migraines. With worsening migraines, she frequently ran out of her monthly allowable six tablets of ZOMIG® 5 mg tablets before month's end. She has gone through migraines relying on EXCEDRIN® to minimally dull the pain. She tried hormone replacement therapy, which also worsened the migraine severity and frequency. She is concerned about the side effects of exhaustion and fatigue associated with most preventive medication. The patient started the method of treatment of the invention by daily doses of the following: coenzyme Q10, 50 mg; vitamin $B_{12}$ 1,000 μg; magnesium, 400 mg; and riboflavin, 50 mg. She reports that on two years of the vitamin regimen her migraines return to the prior frequency and severity, presently two times per month. These migraines do not cause her to miss work and she has an adequate monthly supply of ZOMIG® 5 mg. Her menopausal symptoms of sweats and insomnia still have been occurring during this two year improvement of her migraines on the above stated regimen.

Example 6

Patient RW is 52 year old female with a long standing history of migraines for decades. Her health became complicated six years ago when she was diagnosed with breast cancer and treated with bilateral mastectomy and subsequent reconstructive surgery, breast site radiation therapy, and TAXOL® chemotherapy. (TAXOL® is the registered trademark of Bristol-Myers Squibb Company, New York, N.Y.) Prior to her diagnosis and treatment for breast cancer, her migraines occurred only two to three times per month and responded well to IMITREX® 100 mg orally. Her migraines never interfered with her ability to work and handle activities of living. She was placed on ARIMIDEX® to reduce breast cancer occurrence. (ARIMIDEX is the registered trademark of AstraZeneca UK LTD., London, England, UK.) She feels that ARMIDEX® started to make her migraines more frequent, disabling, and less responsive to abortive, acute migraine therapy of either IMITREX® taken with or without VICODIN®. Her migraines were now occurring ten to twelve times per month. The migraines were associated with photophobia, phonophobia, and nausea with emesis. The most disabling features of the migraine were the symptoms of exhaustion and fatigue that made working impossible. Eventually she stopped taking ARIMIDEX® after four years due to worsening migraines. During this time of worsening migraines, she has had numerous blood tests because of her cancer history and increased clotting tendencies. She had numerous magnetic resonance imaging of the brain as well as a magnetic resonance arteriogram and venogram of the brain. She was placed on TOPAMAX® which was discontinued because it did not reduce migraine frequency, and caused alopecia. She was placed on ELAVIL® 75 mg orally at bedtime, but it did not reduce migraine frequency and caused weight gain. The patient tried LYRICA® but had to stop immediately due to fluid retention and confusion. She tried brief rounds of the steroid prednisone, which gave a short-lived migraine reduction that disappeared when the steroid was stopped. The patient stopped the steroid because of concern over the problematic long term side effects of steroids. Subsequently, the patient started the method of treatment of the invention by daily doses of the following: coenzyme Q10, 50 mg; vitamin $B_{12}$ 1,000 μg; magnesium, 400 mg; and riboflavin, 50 mg. Currently, she also takes ELAVIL® 75 mg at bedtime. Her headaches are now less frequent, down to five times monthly, and more responsive to a single dose of IMITREX® when used as a rescue medication. She briefly tried feverfew for two weeks but stopped taking it over concern of potential side effects. Subsequently, the patient underwent two chemodenervation treatments with BOTOX® 100 units injections (25 units frontalis muscle, 25 units into each temporalis muscles, 25 units into occipital-cervical notch muscles.) At the time of the second treatment, she reported she is back working full time and not needing IMITREX® at all. She states that the regimen disclosed hereinabove along with the BOTOX® injections and ELAVIL® have caused her migraines to be in remission.

In conclusion, herein is presented a dietary supplement and a method of treatment with the dietary supplement for preventing and reducing the occurrence of migraine headaches and the associated symptoms of migraine headaches. The invention is illustrated by the anecdotal evidence of efficacy and safety throughout the written description. It should be understood that numerous variations are possible, while adhering to the inventive concept. Such variations are contemplated as being a part of the present invention.

What is claimed is:

1. A method of treatment to reduce the occurrence of migraine headaches comprising by administering a combination of dietary supplements, wherein the composition consists of 50 mg riboflavin, 400 mg magnesium as magnesium oxide, 1000 μg vitamin $B_{12}$ and 50 mg coenzyme Q10 daily.

2. A method of treatment to reduce the occurrence of a plurality of associated symptoms of migraine headaches comprising administering a combination of dietary supplements, wherein the composition consists of 50 mg riboflavin, 400 mg magnesium as magnesium oxide, 1000 μg vitamin B12 and 50 mg coenzyme Q10 daily.

* * * * *